United States Patent
Kikuchi et al.

(10) Patent No.: US 6,666,871 B2
(45) Date of Patent: Dec. 23, 2003

(54) INSERTION DEVICE FOR DEFORMABLE INTRAOCULAR LENS

(75) Inventors: Toshikazu Kikuchi, Hachioji (JP); Kenichi Kobayashi, Tokyo (JP)

(73) Assignee: Canon-Staar Co. Inc., Tokyo (JP)

( * ) Notice: Subject to any disclaimer, the term of this patent is extended or adjusted under 35 U.S.C. 154(b) by 0 days.

(21) Appl. No.: 10/176,187

(22) Filed: Jun. 20, 2002

(65) Prior Publication Data

US 2003/0139749 A1 Jul. 24, 2003

(30) Foreign Application Priority Data

Jan. 23, 2002 (JP) .................................... 2002-014631

(51) Int. Cl.[7] .................................................. A61F 9/00
(52) U.S. Cl. .................................................... 606/107
(58) Field of Search ............................. 606/107, 108; 623/6.12, 6.11

(56) References Cited

U.S. PATENT DOCUMENTS

| 5,496,328 | A | | 3/1996 | Nakajima et al. |
| 5,722,829 | A | * | 3/1998 | Wilcox et al. ............... 604/22 |
| 6,334,862 | B1 | * | 1/2002 | Vidal et al. ................. 606/107 |
| 6,468,282 | B2 | * | 10/2002 | Kikuchi et al. ............. 606/107 |

FOREIGN PATENT DOCUMENTS

| JP | 58-146346 | 8/1983 |
| JP | 2-212350 | 8/1992 |
| JP | 4-212350 | 8/1992 |
| JP | 5-103803 | 4/1993 |
| JP | 5-103808 | 4/1993 |
| JP | 7-23990 | 1/1995 |
| JP | 7-23991 | 1/1995 |
| JP | 5-103809 | 4/1995 |
| JP | 8-38542 | 2/1996 |
| JP | 9-506285 | 6/1997 |
| JP | 11-510711 | 9/1999 |
| JP | 2000-60880 | 2/2000 |
| JP | 2001104347 | 4/2001 |

* cited by examiner

Primary Examiner—Cary E. O'Connor
Assistant Examiner—Candice C. Melson
(74) Attorney, Agent, or Firm—Roth & Goldman, P.A.

(57) ABSTRACT

An insertion device can deform a deformable intraocular lens into a smaller size and insert the intraocular lens into the eye. The insertion device includes a device body; an insertion tube attached to a front end of the device body and adapted to be inserted into the eye; and a push rod axially movable within the device body and the insertion tube and adapted to insert the intraocular lens into the eye when advanced. A drive member is rotatably provided at a rear end of the push rod. A motion conversion mechanism is disposed between the device body and the drive member and is adapted to axially move the drive member, upon rotation of the drive member, in order to axially move the push rod. A push member is provided at the rear end of the push rod and projects rearward from the drive member.

4 Claims, 3 Drawing Sheets

INSERTION DEVICE FOR DEFORMABLE INTRAOCULAR LENS

BACKGROUND OF THE INVENTION

1. Field of the Invention

The present invention relates to an insertion device for inserting a deformable intraocular lens into the eye. Examples of such a deformable intraocular lens include a deformable intraocular lens that is inserted into the eye in place of the natural lens when the latter is physically extracted because of cataracts, and a vision correction lens that is inserted into the eye for the sole purpose of vision correction.

2. Description of the Related Art

Implantation of an intraocular lens for treating cataract has been widely performed since 1949, when Ridley implanted for the first time an artificial lens; i.e., an intraocular lens, into the human eye in place of an opaqued natural lens during cataract surgery.

As disclosed in Japanese Patent Application Laid-Open (kokai) No. 58-146346, there have been invented improved intraocular lenses which can be inserted into the eye through a small incision formed in the eyeball. In one of the improved intraocular lenses, at least an optical portion is made of a deformable elastic material having a predetermined memory characteristic. In another improved intraocular lens, at least an optical portion is made of an elastic material having a predetermined memory characteristic, and there are provided supports which are made of a material different from that of the optical portion and are adapted to support the optical portion within the eye.

Moreover, as disclosed in Japanese Patent Application Laid-Open (kokai) Nos. 4-212350, 5-103803, 5-103808, 5-103809, and 7-23990, improved insertion tools have been proposed. By use of these tools, the optical portion of an intraocular lens is compressed, rolled, bent, stretched, or folded so as to reduce its exterior size, thereby enabling the intraocular lens to be inserted into the eye through a small incision formed in the eyeball. These insertion tools facilitate an operation for implanting an intraocular lens into the eye.

FIG. 3 and FIGS. 4A and 4B show the conventional deformable intraocular lenses. The deformable intraocular lens 1 shown in FIG. 3 is composed of a circular optical portion 2 and two symmetrically disposed supports 3. The circular optical portion 2 is made of an elastic material having predetermined memory characteristics. The supports 3 are made of a material different from that of the optical portion 2, and bases 3a of the supports 3 are embedded in the peripheral region of the optical portion 2 for fixing, while wire-shaped tails 3b of the supports are curved. The deformable intraocular lens 1 shown FIGS. 4A and 4B is composed of a circular optical portion 2 and a pair of thin plate-shaped support portions 4 that are integral with the optical portion 2. The optical portion 2, like the optical portion 2 shown in FIG. 3, is made of an elastic material having predetermined memory characteristics. The support portions 4 are projected from the periphery of the optical port 2 in opposite directions.

These intraocular lenses 1 are inserted into the eye by use of an insertion device as shown in FIG. 5. The deformable intraocular lens 1 is folded in order to reduce its exterior size and is advanced along an insertion tube in order to be inserted into the eye through an incision formed in the eyeball.

FIG. 5 is a partially cutaway overall perspective view of a conventional insertion device for inserting a deformable intraocular lens.

In FIG. 5, reference numeral 11 denotes the insertion device; 12 denotes a device body; 13 denotes a screw sleeve; 14 denotes a push rod; 15 denotes an enclosing member having a lens receiving section and an open/close mechanism and adapted to deform a deformable intraocular lens into a smaller size; 16 denotes a slide stopper which engages the open/close mechanism so as to maintain the open/close mechanism in a closed state; and 17 denotes an insertion tube.

When the insertion device 11 is used to insert a deformable intraocular lens 1 into the eye through a small incision, the open/close mechanism of the enclosing member 15 of the insertion device 11 is first opened. Subsequently, the deformable intraocular lens 1 is placed on the lens receiving section, and the open/close mechanism is closed so as to reduce the exterior size of the deformable intraocular lens 1. Subsequently, the slide stopper 16 attached to the device body 12 is moved toward the lens receiving section so as to engage the open/close mechanism and bring the same into a closed state. Thus, placement of the intraocular lens 1 into the lens receiving section is completed.

Subsequently, the screw sleeve 13, disposed at the rear of the device body 12, is moved toward the device body 12, brought into engagement with a screw portion 12b formed on the device body 12, and rotated in order to advance the push rod 14, to thereby push forward the deformable intraocular lens 1 from the lens receiving section. As a result, the deformable intraocular lens 1 is inserted into the eye through the tip end of an insertion tube 17 provided at the front end of the lens receiving section, which tip end has been inserted into the eye through a small incision formed in the eyeball.

Japanese Kohyo (PCT) Patent Publication No. 11-510711 discloses another conventional insertion device. In this insertion device, an intraocular lens is advanced within an insertion tube by mean of advancing movement of a push rod caused by an operation of pushing a plunger.

In the conventional insertion device shown in FIG. 5, when an operator wishes to advance an intraocular lens within the insertion tube, the operator must rotate the screw sleeve with one hand in order to advance the push rod, while holding the device body with the other hand. That is, the operator must use both hands to operate the insertion device in the course of an operation during which the operator must use various operation tools. Therefore, the necessity of using both hands hinders the ease of use during the operation.

In the conventional insertion device in which the push rod is advanced through an operation of pushing a plunger, since a pressing force is applied to the plunger along a straight direction, performing fine adjustment in relation to advancing movement of the push rod requires a great deal of skill.

SUMMARY OF THE INVENTION

An object of the present invention is to provide an insertion device for a deformable intraocular lens, which device allows an operator to use a single hand or both hands for operation of pushing an intraocular lens into the eye.

In order to achieve the above object, the present invention provides an insertion device for deforming a deformable intraocular lens into a smaller size and inserting the intraocular lens into the eye, comprising a device body; an insertion tube attached to a front end of the device body and adapted to be inserted into the eye; a push rod axially movable through the device body and the insertion tube and adapted to insert the intraocular lens into the eye when advanced; a drive member rotatably provided at a rear end of the push rod; a motion conversion mechanism disposed between the device body and the drive member and adapted to axially move the drive member, upon rotation of the drive member, in order to axially move the push rod; and a push member provided at the rear end of the push rod and projecting rearward from the drive member. Preferably, the motion conversion mechanism includes a male screw formed on a rear end portion of the device body and a female screw formed on the drive member and in screw engagement with the male screw.

By virtue of the structure as described above, the operation of inserting an intraocular lens into the eye can be performed by use of a single hand or both hands. That is, one-hand operation or two-hand operation can be selectively used in accordance with the conditions of the operation. Therefore, ease of operation of the insertion device can be improved.

Preferably, the device body includes adjustment means for adjusting resisting force against the axial movement of the push rod. More preferably, the adjustment means is an elastic member which generates frictional resistance.

In this case, the force required to insert an intraocular lens can be adjusted to a desired level, thereby providing operation feeling suitable for surgery which requires delicate operations.

BRIEF DESCRIPTION OF THE DRAWINGS

Various other objects, features and many of the attendant advantages of the present invention will be readily appreciated as the same becomes better understood by reference to the following detailed description of the preferred embodiment when considered in connection with the accompanying drawings, in which.

DETAILED DESCRIPTION OF PREFERRED EMBODIMENT

An embodiment of the present invention will be described with reference to the accompanying drawings.

Figure 1:
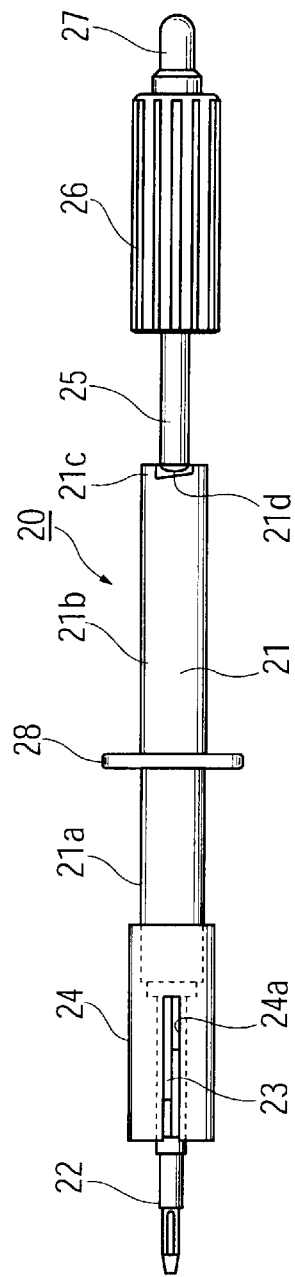
FIG. 1 is a plan view of an insertion device for a deformable intraocular lens according to an embodiment of the present invention.
Figure 2:
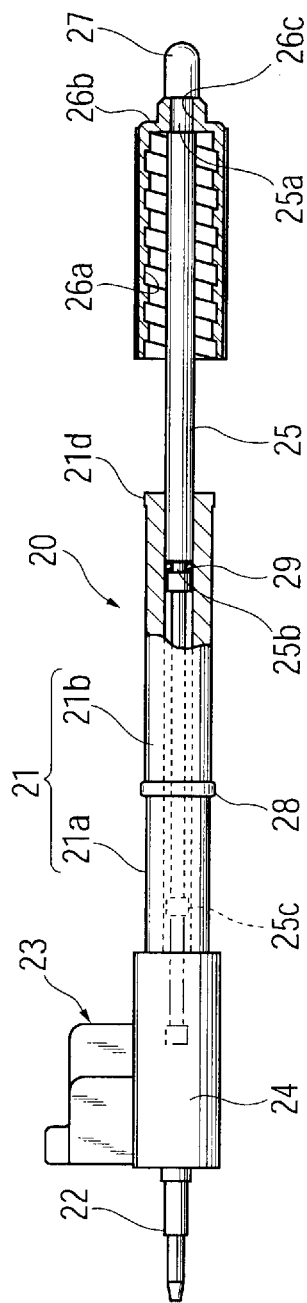
FIG. 2 is a partially cutaway side view of the insertion device of FIG. 1.
Figure 3:
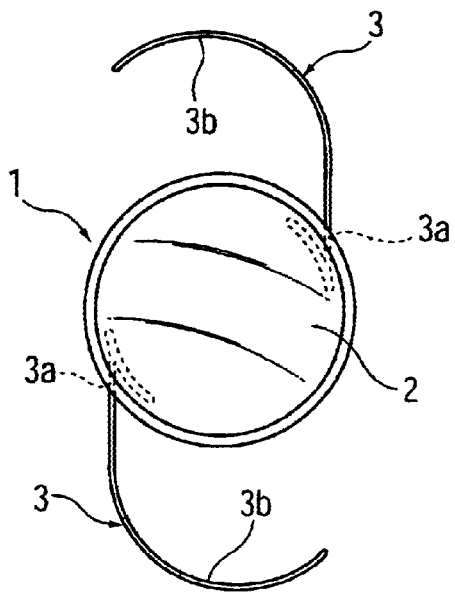
FIG. 3 is a plan view of an example deformable intraocular lens.
Figure 4A:
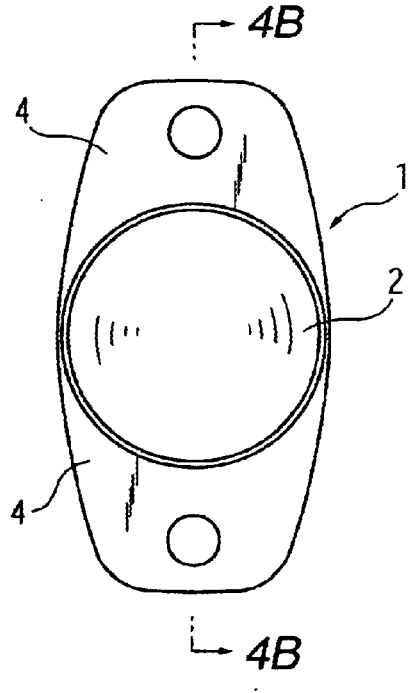
FIG. 4A is a plan view of another example deformable intraocular lens.
Figure 4B:
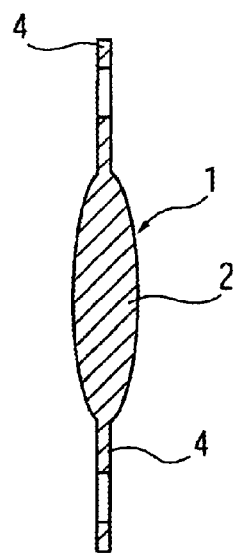
FIG. 4B is a cross sectional view taken along line 4B—4B of FIG. 4A.
Figure 5:
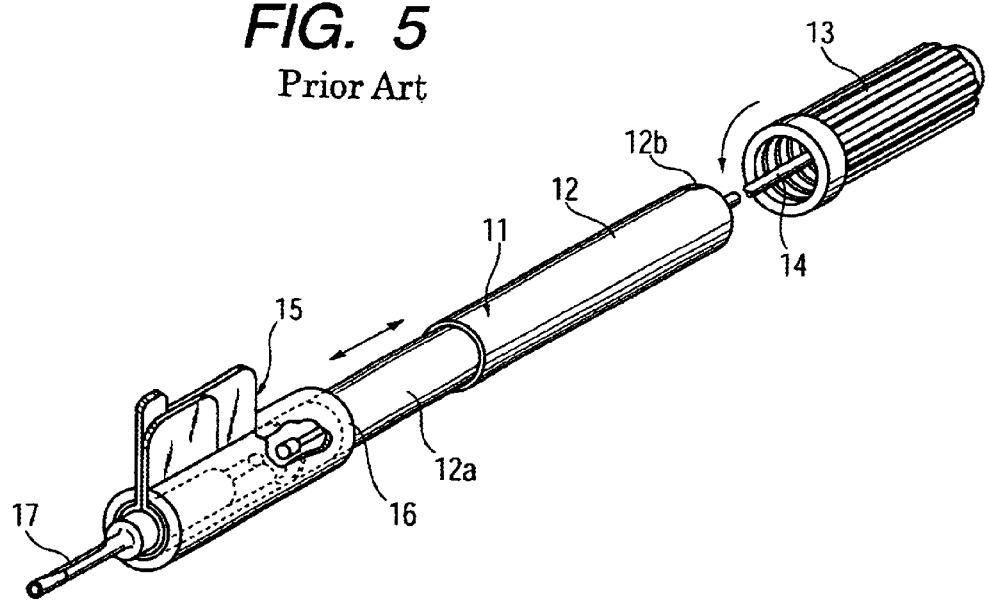
FIG. 5 is a perspective view of a conventional insertion device for a deformable intraocular lens.

FIG. 1 is a plan view of an insertion device for a deformable intraocular lens according to an embodiment of the present invention; and FIG. 2 is a partially cutaway side view of the insertion device.

In these drawings, reference numeral 20 denotes an insertion device which includes a device body 21 having a smaller diameter portion 21a at the front end side and a larger diameter portion 21b at the rear end side. An insertion tube 22 is fixed to the front end of the device body 21 in such a manner that an axially extending inner cavity of the insertion tube 22 is aligned with an axially extending inner cavity of the device body 21. An enclosing member 23 is provided on the insertion tube 22. The enclosing member 23 has a lens receiving section and an open/close mechanism and adapted to reduce the exterior size of a deformable intraocular lens. A cylindrical slide stopper 24 is slidably fitted onto the front-end side, smaller diameter portion 21a of the device body 21. The enclosing member 23 is opened and closed by an operator, and is maintained in a closed state by the slide stopper 24. Moreover, a push rod 25 is accommodated within the inner cavity of the device body 21 and that of the insertion tube 22; and a screw sleeve 26 serving as a drive member for moving the push rod 25 back and forth is provided on the rear end side of the device body 21. The insertion device of the present embodiment has substantially the same structure as that of the insertion device disclosed in Japanese Patent Application No. 10-239124 (Japanese Patent Application Laid-Open (kokai) No. 12-60880) whose assignee is the also the assignee of the present application, except that the insertion device of the present embodiment includes an push member 27 for advancing the push rod 25 independently of rotational motion of the screw section; a projection 28 provided at an approximately central portion of the device body 21 to project radially outward from the outer peripheral surface thereof (i.e., to extend outward perpendicularly to the axis of the device body 21); and an elastic member 29 disposed at a substantially central portion of the push rod 25 with respect the longitudinal direction thereof and serving as adjustment means. The entire description of Japanese Patent Application No. 10-239124 (Japanese Patent Application Laid-Open (kokai) No. 12-60880) is herein incorporated by reference.

The device body 21 has a male screw 21d formed on the outer circumferential surface of a rear end portion 21c. The male screw 21d is brought into screw engagement with a female screw 26a formed on the inner circumferential surface of the screw sleeve 26, which serves as a drive member for moving the push rod 25. The male screw 21d and the female screw 26a constitute a motion conversion mechanism for converting rotational motion of the screw sleeve 26 to axial motion of the push rod 25.

A through-hole 26c, which is slightly smaller in diameter than the push rod 25, is formed at the center of an end wall portion 26b of the screw sleeve 26. A smaller-diameter shaft portion 25a extending from the rear end of the push rod 25 is rotatably received by the through-hole 26c, so that the screw sleeve 26 can be rotated independently of the push rod 25. The smaller-diameter shaft portion 25a projects rearward from the end wall portion 26b of the screw sleeve 26; and a push member 27 is attached to the projecting portion of the smaller-diameter shaft portion 25a. Therefore, the push member 27 is located on the rear side with respect to the end wall portion 26b of the screw sleeve 26. Accordingly, the push rod 25 can be moved back and force through an operation of rotating the screw sleeve 26. In addition, the push rod 25 can be advanced through an operation of pushing the push member 27 frontward, which causes the screw sleeve 26 to rotate to thereby advance the push rod 25.

The projection 28, which is provided at an approximately central portion of the device body 21, is formed integrally with the device body 21 such that the projection 28 has an elliptical shape and projects from the outer circumferential surface of the device body 21 toward the upper and lower sides thereof in FIG. 1. The elastic member 29, which is disposed at a substantially central portion of the push rod 25 and serves as adjustment means, is formed into a ring shape by use of a rubber material such as nitrile rubber, butyl rubber, silicon rubber, or Teflon (registered trademark) rubber. The elastic member 29 is accommodated within a circumferential groove 25b formed at a substantially central portion of the push rod 25 with respect to the longitudinal direction thereof, and the outer circumferential surface of the elastic member (elastic ring) 29 is in contact with the inner wall surface of the device body 21 to thereby generate frictional resistance.

A tip end portion 25c of the push rod 25 is formed to have a large diameter suitable for pushing out the intraocular lens 1. The enclosing member 23, which is adapted to accommodate the intraocular lens 1 folded to a smaller size, is coupled to the front end portion of the device body 21. By means of a known structure, the enclosing member 23 allows an operator to set the intraocular lens 1 on the lens receiving section of the enclosing member 23 in an opened state, and then close the enclosing member 23 in order to enclose the intraocular lens 1 while folding the same.

The slide stopper 24 is fitted onto the device body 21 in such a manner that the cylindrical slide stopper 24 can move axially but cannot rotate about the axis. The slide stopper 24 maintains the enclosing member 23 in a closed state by means of a groove 24a formed in the slide stopper 24. The device body 21, the screw sleeve 25, the push rod 26, the enclosing member 23, and the insertion tube 22 formed integrally with the enclosing member 23 are each formed of a synthetic resin.

Next, a manner of use of the intraocular lens insertion device configured as described above will be described.

First, an operator advances the screw sleeve 26 up to a point at which the screw sleeve 26 comes into contact with the rear end of the device body 21, and brings the screw sleeve 26 into screw engagement with the male screw portion 21d formed at the rear end portion of the device body 21. Subsequently, as in the case of using an injection syringe, the operator holds the insertion device with one hand, while engaging with his or her fingers with the handguard-shaped projection 28 of the device body 21 and the push member 27, which projects outward from the end wall portion 26b of the screw sleeve 26. In this state, the operator pushes the push member 27 so as to advance the push rod 25. At this time, the screw sleeve 26, which is rotatably engaged with the push rod 25, advances, while rotating, so as to follow the advancing movement of the push rod 25.

As a result, the intraocular lens 1 is advanced through the insertion tube 22 and inserted into the eye from the opening formed at a tapered tip end of the insertion tube 22. Due to the elastic restoration force of the optical portion 2 of the intraocular lens 1, the intraocular lens 1 inserted into the eye is restored to its original shape when discharged from the insertion tube 22.

In the above-described embodiment, the elliptical projection 28, which is provided at an approximately central portion of the device body 21, is formed integrally with the device body 21. This configuration may be modified in such a manner that a projection 28 having a circular handguard-like shape is formed separately, and attached to a stepped portion at an approximately central portion of the device body by means of welding, bonding, or any other suitable means.

In the above-described embodiment, a method of operating the insertion device with a single hand has been described. However, as in the case of conventional insertion devices, the insertion device of the present invention can be operated by use of both hands; i.e., an operator rotates the screw sleeve so as to advance and retract the push rod by use of one hand, while holding the device body with the other hand.

As described above, the operation of inserting an intraocular lens, which has conventionally required two-hand operation, can be performed by use of a single hand or both hands. That is, one-hand operation or two-hand operation can be selectively used in accordance with the conditions of the operation. Therefore, ease of operation of the insertion device can be improved.

Further, since the elastic member such an O-ring is disposed between the inner wall surface of the device body and the outer circumferential surface of the push rod to thereby generate frictional force, the force required to insert an intraocular lens can be adjusted to a desired level, thereby providing operation feeling suitable for surgery which requires delicate operations.

Obviously, numerous modifications and variations of the present invention are possible in light of the above teachings. It is therefore to be understood that within the scope of the appended claims, the present invention may be practiced otherwise than as specifically described herein.

What is claimed is:

1. An insertion device for deforming a deformable intraocular lens into a smaller size and inserting the intraocular lens into an eye, comprising:

a device body;

an insertion tube attached to a front end of the device body and adapted to be inserted into the eye;

a push rod axially moveable through the device body and the insertion tube and adapted to insert the intraocular lens into the eye when advanced;

a rotatable drive member at a near end of the push rod;

a motion conversion mechanism disposed between the device body and the drive member and adapted to axially move the drive member, upon rotation of the drive member, in order to axially move the push rod; and an axially moveable push member provided at the rear end of the push rod and projecting rearward from the rotatable drive member for axially advancing the push rod without rotating the push member or push rod.

2. An insertion device according to claim 1, wherein the motion conversion mechanism includes a male screw formed on a rear end portion of the device body and a female screw formed on the drive member and in screw engagement with the male screw.

3. An insertion device according to claim 1, further comprising adjustment means for adjusting resisting force against axial movement of the push rod.

4. An insertion device according to claim 3, wherein the adjustment means is an elastic member which generates frictional resistance.

* * * * *